US012622750B2

(12) United States Patent
　　Stevenson

(10) Patent No.: US 12,622,750 B2
(45) Date of Patent: May 12, 2026

(54) METHOD AND APPARATUS FOR PLANNING PLACEMENT OF AN IMPLANT

(71) Applicant: Medtronic Navigation, Inc., Louisville, CO (US)

(72) Inventor: Tyler S. Stevenson, Westminster, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 230 days.

(21) Appl. No.: 17/975,095

(22) Filed: Oct. 27, 2022

(65) Prior Publication Data

US 2024/0138914 A1　　May 2, 2024

(51) Int. Cl.
　　*A61B 34/10* 　　(2016.01)
　　*A61B 34/20* 　　(2016.01)
　　*G16H 30/40* 　　(2018.01)
　　*A61N 1/05* 　　(2006.01)

(52) U.S. Cl.
　　CPC ............. *A61B 34/10* (2016.02); *A61B 34/20* (2016.02); *G16H 30/40* (2018.01); *A61B 2034/107* (2016.02); *A61N 1/0534* (2013.01)

(58) Field of Classification Search
　　CPC ... A61B 34/10; A61B 34/20; A61B 2034/107; A61B 34/25; A61B 2034/102; A61B 2034/2051; A61B 2034/2055; A61B 2090/3762; G16H 30/40; A61N 1/0534
　　See application file for complete search history.

(56) References Cited

U.S. PATENT DOCUMENTS

| 5,592,939 | A | 1/1997 | Martinelli |
| 5,913,820 | A | 6/1999 | Bladen et al. |
| 5,983,126 | A | 11/1999 | Wittkampf |
| 6,474,341 | B1 | 11/2002 | Hunter et al. |
| 6,747,539 | B1 | 6/2004 | Martinelli |
| 6,940,941 | B2 | 9/2005 | Gregerson et al. |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 7,751,865 | B2 | 7/2010 | Jascob et al. |
| 7,797,032 | B2 | 9/2010 | Martinelli et al. |

(Continued)

FOREIGN PATENT DOCUMENTS

| WO | 2016019129 A1 | 2/2016 |
| WO | 2018/008034 A2 | 1/2018 |

(Continued)

OTHER PUBLICATIONS

International Search Report and Written Opinion for related International Application No. PCT/IB2023/060581; date of mailing: Jan. 25, 2024; 15 pages.

(Continued)

*Primary Examiner* — Kambiz Abdi
*Assistant Examiner* — Tran N Nguyen

(57) ABSTRACT

Disclosed is a system to plan and position an implant in a subject. The planned position may be based upon various features and structures identified in a group of subjects for a current subject. The implant may then be positioned in a selected position including a relative position and orientation of one or more electrodes on the implant which may be identified as an optimal position for the selected current subject.

20 Claims, 6 Drawing Sheets

(56) References Cited

U.S. PATENT DOCUMENTS

| | | | |
|---|---|---|---|
| 8,160,677 B2 | 4/2012 | Gielen et al. | |
| 9,737,235 B2 | 8/2017 | Hartmann | |
| 10,881,371 B2 | 1/2021 | Helm et al. | |
| 11,071,507 B2 | 7/2021 | Helm et al. | |
| 11,344,268 B2 | 5/2022 | Garlow et al. | |
| 11,399,784 B2 | 8/2022 | Garlow et al. | |
| 11,412,951 B2 | 8/2022 | Piron et al. | |
| 2004/0116803 A1 | 6/2004 | Jascob et al. | |
| 2010/0191088 A1* | 7/2010 | Anderson | A61B 34/20 |
| | | | 606/300 |
| 2010/0249657 A1* | 9/2010 | Nycz | A61B 90/06 |
| | | | 606/53 |
| 2011/0264165 A1* | 10/2011 | Molnar | A61N 1/36185 |
| | | | 607/45 |
| 2011/0268325 A1* | 11/2011 | Teichman | A61B 34/20 |
| | | | 382/128 |
| 2012/0099768 A1 | 4/2012 | Helm et al. | |
| 2012/0226481 A1* | 9/2012 | Carson | A61B 34/20 |
| | | | 703/1 |
| 2016/0135816 A1* | 5/2016 | Lavallee | B25J 9/0009 |
| | | | 606/88 |
| 2017/0000505 A1* | 1/2017 | Gordon | A61B 17/1739 |
| 2018/0217734 A1 | 8/2018 | Koenig et al. | |
| 2019/0175291 A1* | 6/2019 | Hagag | A61B 34/20 |
| 2019/0240489 A1 | 8/2019 | Tsay et al. | |
| 2022/0022968 A1* | 1/2022 | Brisson | A61B 34/30 |
| 2022/0125515 A1 | 4/2022 | Mcguan et al. | |
| 2022/0151537 A1 | 5/2022 | Naor et al. | |
| 2022/0241023 A1 | 8/2022 | Bergman et al. | |

FOREIGN PATENT DOCUMENTS

| | | |
|---|---|---|
| WO | 2018/008034 A3 | 2/2018 |
| WO | 2022211976 A1 | 10/2022 |

OTHER PUBLICATIONS

International Search Report and Written Opinion for related International Application No. PCT/IB2023/060615; mailed: Jan. 23, 2024; 13 pages.

* cited by examiner

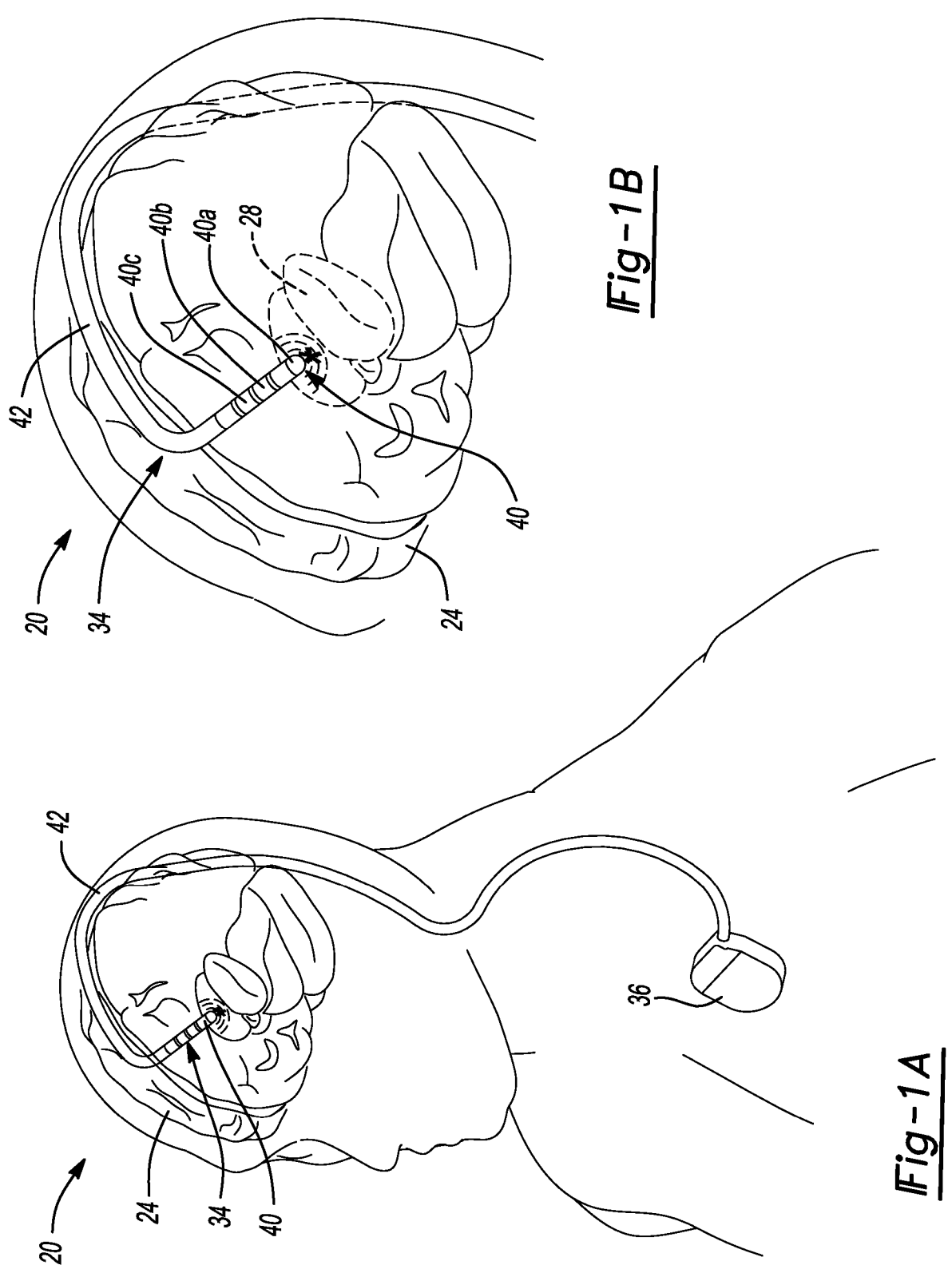
_Fig-1B_
_Fig-1A_

METHOD AND APPARATUS FOR PLANNING PLACEMENT OF AN IMPLANT

FIELD

The present disclosure is related to a system for planning a procedure on a subject, such as evaluating one or more placements (e.g., existing placements and stimulation regions or previously implanted) and stimulation regions in one or more subjects for planning a future procedure.

BACKGROUND

This section provides background information related to the present disclosure which is not necessarily prior art.

In performing a procedure on a human subject, implants may be positioned in the human subject for various purposes. For example, an implant may be positioned within a brain of a human to provide stimulation or therapy at selected positions therein. Therapy within the brain, however, may vary in efficacy, speed, and the like based upon various parameters of the implantation including implantation location, brain network specifics, delivery features, or the like.

According to various systems, an implant may be positioned within a subject to provide therapy thereto. The therapy may include electrical stimulation of portions of the brain adjacent to the implant. In various embodiments, for example, diffusion tensor image data may be used during a selected portion of a procedure, as disclosed in U.S. Pat. No. 8,532,741. In various embodiments, a non-electrical stimulation may also be provided through an implant or an instrument, such as the delivery of a pharmaceutical agent. The pharmaceutical agent may be delivered with a selected device and various image data may be analyzed to assist in determining a placement or delivery location for the pharmaceutical, such as disclosed at U.S. Pat. No. 8,335,552.

SUMMARY

This section provides a general summary of the disclosure, and is not a comprehensive disclosure of its full scope or all of its features.

A portion of a subject, such as a human anatomy, can be imaged to generate image data thereof that may be analyzed as data and/or visually by a user. It is understood, however, that a subject may include a non-human subject and/or non-living subject. Non-living subjects may include enclosed structures such as wings, robotic systems, etc. In analyzing the image data, various features may be identified and/or used to identify various additional features. For example, an anatomical landmark may be identifiable in a selected image data and may be used to assist in identifying a region or portion of image data that is not visually distinguishable therefrom. Various types of image data may include magnetic resonance imaging (MRI) data, x-ray image data, functional MRI data, diffusion data (such as MRI DTI data), and the like. For example, an anterior commissure and a posterior commissure may be identified in image data to assist in locating and/or approximating locations of a sub-thalamic nucleus in the image based upon a pre-determined co-location of the sub-thalamic nucleus relative to the anterior commissure and the posterior commissure such as disclosed at U.S. Pat. No. 8,160,677, incorporated herein by reference.

In various embodiments, an implant may be positioned relative to an identified feature in the image. The implant may include a deep-brain stimulation (DBS) device. The DBS may also be referred to as and/or understood as a neuromodulation device. A stimulation to the brain, as discussed herein, may be a stimulation including an electrical stimulation, such as an application of a voltage, amperage, etc. As used herein, stimulation, including electrical stimulation may refer to neuromodulation. Thus, stimulation may result in excitatory or inhibitory response in a brain network. The treatment device, such as the DBS, may be used to provide therapy to a subject. In various embodiments, features identified in the image data may include an anterior nucleus of the thalamus (ANT) also referred to as the anterior thalamic nucleus (ATN). Stimulation of the ANT and/or portions of the brain relative to the ANT may assist in therapy for patients diagnosed with various conditions, e.g., epilepsy. In particular, a treatment, such as a stimulation, may assist in epilepsy treatment or therapy for patients that are pharmaco-resistant. Accordingly, analysis of image data may assist in identifying the ANT and/or portions of the brain relative to the ANT. These portions may be used for various purposes, such as therapy of epilepsy.

A system is disclosed that is able to receive data, such as real time acquisition and/or transfer to a processor module. The received data may be used to make a determination based upon the data. The data may include inputs such as a type of procedure, positioning of an implant during a procedure, and use of the implant after the implantation procedure. Inputs may also include an outcome that are related to or specified for each of the other inputs. A correlation may be made based upon the outcome to the inputs.

A further procedure, such as a current patient or current subject procedure, may be planned based upon the determined correlation. The determined correlation may be recalled into a planning procedure to assist in planning a current procedure. The planned procedure may then be performed with the assistance of various other systems. For example, a surgical navigation system may be used to assist in performing a planned procedure on a current to the subject.

Therefore, the planned procedure may be performed on the subject. The planned procedure may be based upon a correlation of previous outcomes in light of specific inputs, including a pose of an implant and volumes of activation. The navigation system may assist in attempting to re-create specific poses of the implant and a current procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A is a schematic illustration of a subject and implant device;

FIG. 1B is a schematic illustration of a subject and implant device;

Corresponding reference numerals indicate corresponding parts throughout the several views of the drawings.

DETAILED DESCRIPTION

Figure 2:
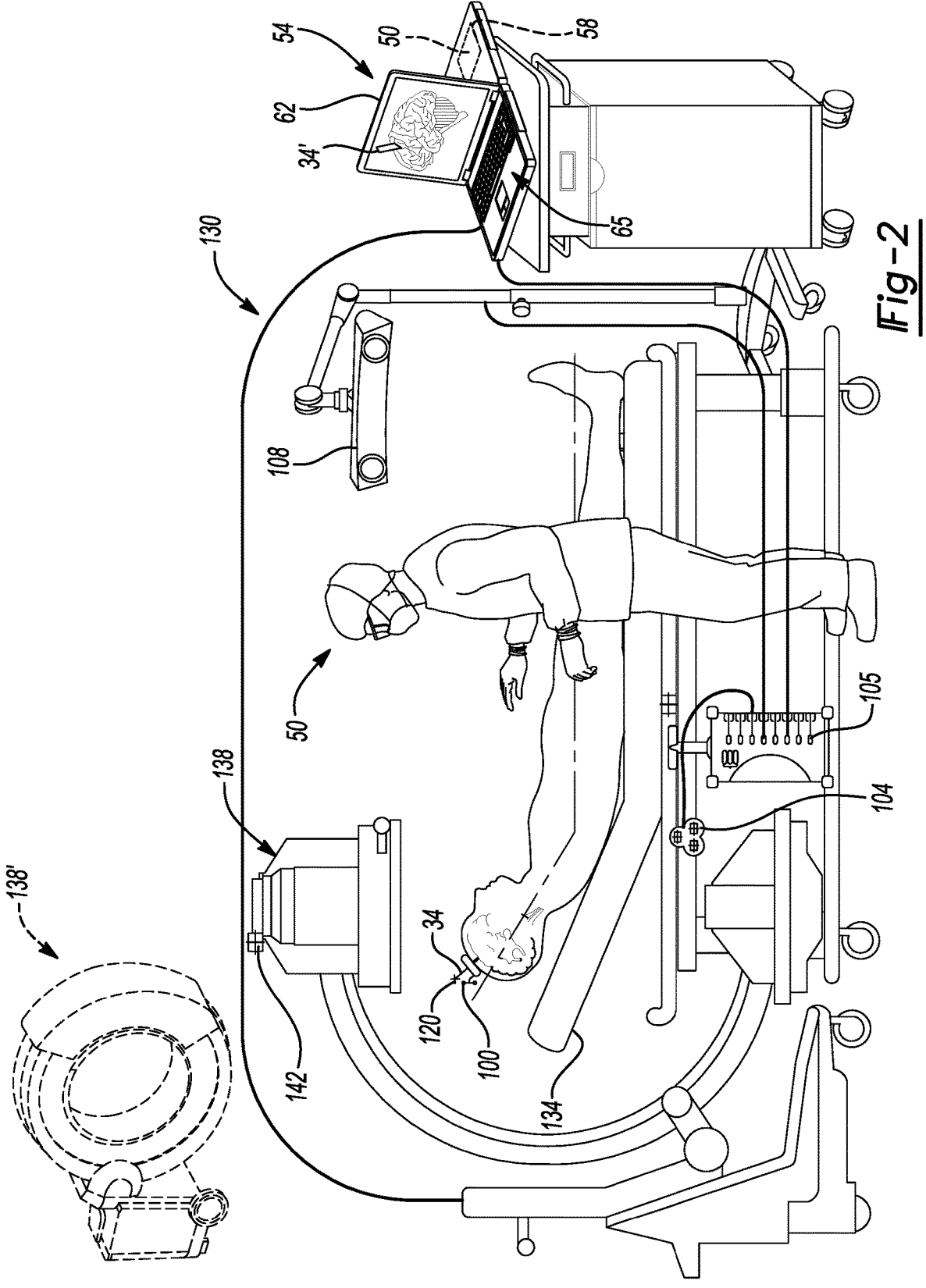
FIG. 2 is an environmental view of an operating suite.

Example embodiments will now be described more fully with reference to the accompanying drawings.

With initial reference to FIG. 1A and FIG. 1B, a subject 20 may be any appropriate subject. Although the following discussion relates to a human subject, it is understood that any appropriate living or non-living subject may be provided or be within the scope of the subject disclosure. For example, a non-human living subject may be evaluated and a selected procedure performed thereon. Further, various non-living subjects may have image data acquired of internal portions and a procedure may be determined, planned, and performed within an outer housing or body (such as a hull) of the non-living subject. Various non-living subjects include internal portions of motors, hulls, or other appropriate subjects. Also, while the following discussion refers exemplarily to placing a deep brain stimulation (DBS) device as an implant for stimulation of a brain, other appropriate implants and/or therapies are within the scope of the subject disclosure.

As noted above, for example, a human subject (also referred to herein as subject) may have a select treatment prescribed therefor. The treatment may include providing various implants into the subject 20, such as into a brain 24 thereof to assist in providing a therapy to the subject. In various embodiments, for example, the subject 20 may be diagnosed with epilepsy or other movement disorders and stimulation may be selected for treating or preventing a therapy to the subject 20.

In various embodiments, a thalamus 28 may be identified and/or a selected portion thereof, such as an interior portion (e.g., anterior nucleus of the thalamus (ANT) also referred to as an anterior thalamic nucleus (ATN)) may be identified for treatment with a selected therapy. In various embodiments, an implant 34 may be positioned relative to selected portions of the brain, such as the thalamus 28 or other appropriate portions in the brain 24 of the subject 20. The implant 34 may be any appropriate implant and may include a deep-brain stimulation probe or implant such as a SEN-SIGHT® DBS lead, sold by Medtronic, Inc. having a place of business in Minnesota. It is understood, however, that other appropriate DBS leads may be used for positioning within the subject 20 and a SENSIGHT® DBS lead is merely exemplary. Further, the lead 34 may include one or more electrodes 40, as discussed herein, and a connector 42 that is connected to a selected stimulator or tremor control device, such as a Percept® or Activa® stimulator or tremor control device (sold by Medtronic, Inc.), or other appropriate neurostimulator to provide a stimulation therapy to the subject 20. The stimulator 36 may be programmed in any appropriate manner, such as discussed further herein, to provide a selected therapy to the subject 20. The programming of the stimulator 36 may be based upon various selections and/or determinations, as also discussed further herein, to provide a selected therapy to the subject 20.

With continuing reference to FIGS. 1A and 1B, and turning reference to FIG. 2, a process for identifying and selecting a placement and/or therapy to be provided to a subject 20 may include positioning the implant 34 and programming of the stimulation, as is understood by one skilled in the art. The process may be carried out as instructions being executed with a selected processor module 50 that accesses selected memory and or input from a user 52. The processor module may be a general purpose processor and/or an application specific processor module. The processor module 50 may be included in and/or accessed by an exemplary processor system 54 may include a processor module 50 and a memory module 58. An output may also be made and may include a display device 62.

The processor module 50 can execute instructions for various sub-processes and portions, including those that are optional. Further, the implant 36 may include one or more processors modules, memory, a power source, etc. Thus, the implant 36 may be programmed such as selecting or storing instructions to be executed by the processor module of the implant. The programming may be selected and/or input to provide a selected stimulation, also referred to as modulation, to the patient 20.

Figures 3A, 3B, 3C:
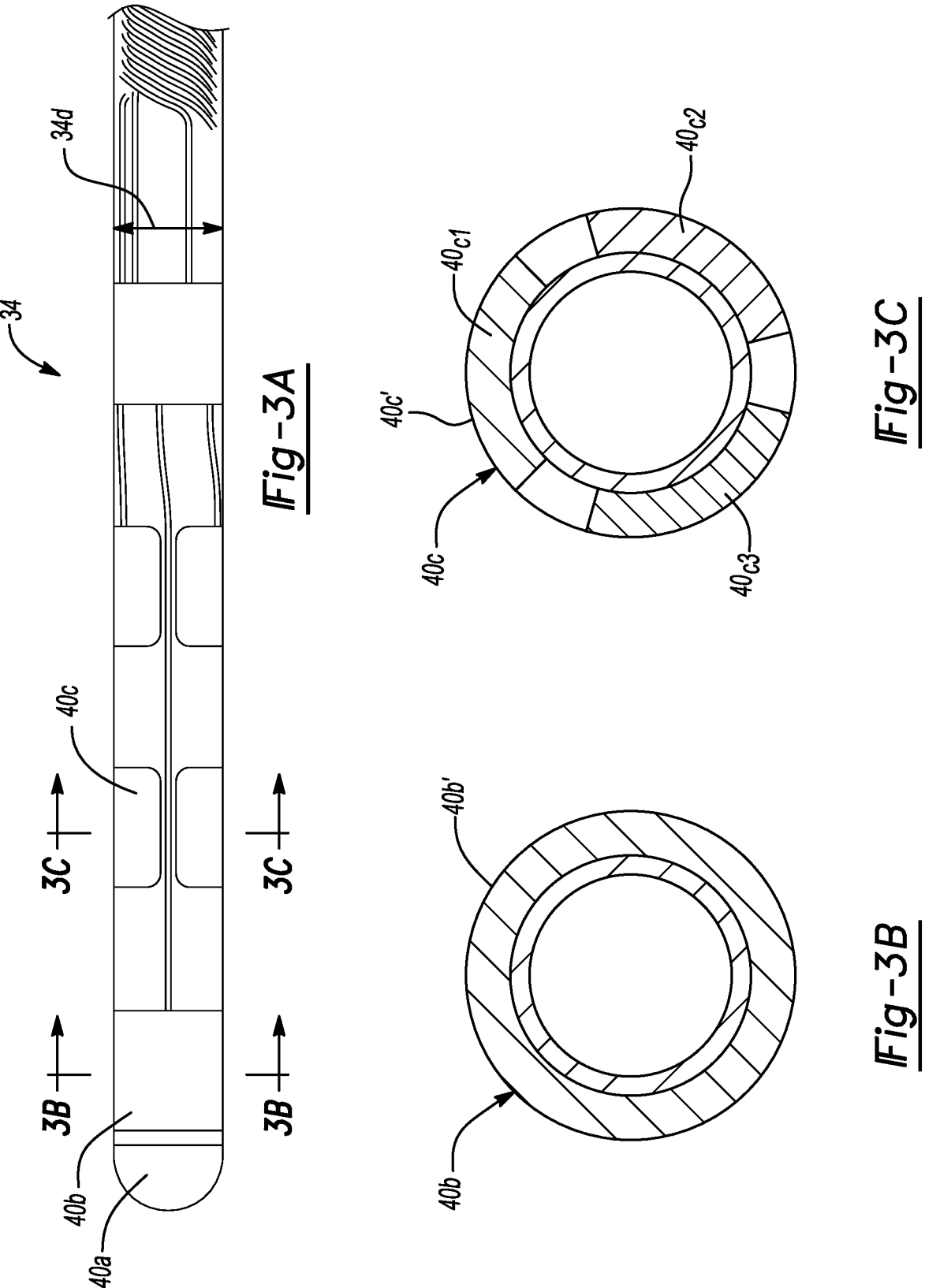
FIG. 3A is a detail view of an implant, according to various embodiments.
FIG. 3B is a cross-sectional view of the implant of FIG. 3A along lines 3B-3B.
FIG. 3C is a cross-sectional view of the implant of FIG. 3A along lines 3C-3C.

With continuing reference to FIGS. 1A and 1B and additional reference to FIGS. 3A and 3B, the implant 34 may include one or a plurality of the electrodes 40. If more than one electrode is provided on the implant, each may be different or the same. For example, the electrode 40 may include three electrodes. For example, a tip electrode 40a, a continuous ring electrode 40b, and a discontinuous or segmented ring electrode 40c. The three electrodes 40a, 40b, and 40c may each be solid or segmented, if selected. The segmented electrodes allow for a plurality of foci for each of the electrodes 40. It is further understood, more or fewer electrodes may be provided and/or more or less than three segments may be provided for the electrodes 40. Regardless, the electrodes 40 may provide a selected and/or directed stimulation. Further, the electrodes 40 may also be referred to as contacts 40. The electrodes or contacts 40 are generally the conductive portions that contact the subject to provide the stimulation.

Briefly, the implant 34 including the various electrode portions or contacts 40, can have at various different contacts and/or modulations, as briefly mentioned above. The tip electrode 40a may be substantially hemispherical or partially spherical and contact tissue along its entire surface. The continuous ring electrode 40b may include a single electrode contact that completely surrounds the implant 34. The implant 34 may include a selected outer dimension, which may be substantially cylindrical such that the implant 34 has a diameter 34d. The electrode or contact 40b may have an outer surface 40b' that is equal to the diameter 34d. The electric contact 40c may have a plurality of contact nodes including a first contact node 40c1, a second contact node 40c2, and the third contact node 40c3 have an external surface 40c' may be defined by all of the electrode nodes and be equal to the diameter 34d. Again, as is understood by one skilled in the art and its discussed further herein each of the contact nodes and 40c1, 40c2, and 40c3 may be selectively energized to provide a treatment to the subject 20, including neuromodulation thereof.

Briefly, the electrodes 40 individually and/or cooperatively (e.g., together, sequenced, etc.) may be programmed and operated to provide a selected volume of activation therapy (VAT) to the subject 20. The VAT may be the region that is directly stimulated and/or modulated due to the stimulation. The VAT are based upon an activation volume due to an activation of a selected portion of the subject or studied subjects based upon the implant 34. The implant 34 includes one or more of the electrodes and/or electrode contacts 40, such as the tip electrode 40a. The electrode 40a may be activated and generate a region of activation that may be referred to or be identified as a boundary of an activated region 70 when the implant 34 and/or portions thereof, such as the electrode 40a, is at a target position 72. The boundary of the activated region 70 may identify those portions in the subject that are activated by the application of the therapy from the electrode. The boundary of the activated region 70 may be various shapes, including two dimensional and/or three dimensional shapes including spherical, partially spherical, and/or other regular or irregular shapes. It is understood, as discussed herein, that various electrodes may include selected activated regions and/or more than one electrode may be used to provide a therapy to form an activated region. Exemplary therapies may include a stimulation of about 0.5 to about 10-volt amplitude, a frequency of about 50 to about 150 Hz, and about a 10 to about a 150 microsecond pulse width. The volume stimulated may be defined by the boundary 70. The simulated boundary 70 may be based upon selected features adjacent to the electrode 40a, and other constraints. Nevertheless, the determined boundary of activation 70 may be identified by a graphical representation that is displayed and/or superimposed on an image of the subject 20 which may be displayed on the display 62.

With continuing reference to FIG. 2, the subject 20 may have the implant 34 positioned therein to assist in providing a therapy to the subject 20. The implant 34 may be positioned within the subject 20 by the user 52. The processing system 50 may assist in evaluating the planning for placement of the implant 34. Further, the processing system 50 and/or various additional systems may also be used to assist in performing the procedure on the subject 20. In various embodiments, including those discussed herein, the implant 34 may be positioned in the subject 20 in an appropriate manner. In various embodiments, for example, the implant 34 may be guided into the subject 20 with the selected navigation system, such as a surgical navigation system including those sold by Medtronic Navigation, Inc. such as the StealthStation® surgical navigation system.

Briefly, in surgical navigation, the subject may be tracked with a selected tracking device, such as a subject tracking device 100. The subject tracking device 100 may be tracked with an appropriate tracking system such as an electromagnetic tracking system 104 and/or an optical tracking system 108. It is understood that other appropriate tracking systems may be used and the EM 104 and optical 108 tracking systems are merely exemplary.

The tracking systems may track the position of the patient tracker 100 and maintain a registration of a patient space to another selected space, such as an image space, to track and determine a relative pose of the patient tracking device 100 to an image displayed on the display 62, such as a subject image 110. A device representation, such as a graphical representation thereof, 34' may be displayed on the display device 62 relative to the subject image 110 based upon a tracked location of the device 34. A device tracking device 120 may be tracked with the tracking system 104, 108, as is understood by one skilled in the art. It is also understood by one skilled in the art that the tracked position and navigated position of the device 34 may be performed based upon a registration of the image or image space 110 to the subject or subject space of the subject 20. As discussed herein, various registrations may also occur between the subject image 110 and/or additional image, such as structures various different image modalities.

The positioning of the device 34 may be performed in a selected suite, such as a surgical suite 130. The surgical suite may include selected structures or portions such as a patient support 134 and an imaging system 138. The imaging system 138 may be used to generate or acquire image data of the subject 20, according to various embodiments. The imaging system 138 may also be tracked with an imaging system tracker 142, as is generally understood by one skilled in the art. Various imaging systems may include an O-arm® imaging system 138', sold by Medtronic, Inc. Thus, the implant 34 may be positioned within the subject 20 based upon the plan or target location, such as identified with the processor module 50, as discussed above. The image data of the subject 20 may be acquired with any appropriate imaging system, such as the imaging systems 138, 138' at any appropriate time such as prior to the procedure, during the procedure, and/or after the procedure. Further, the tracking systems and/or the various tracking devices may be incorporated into a surgical navigation system, according to various embodiments.

To assist in a procedure, an image data of the subject 20 may be acquired with the appropriate imaging system 138, 138'. The imaging system 138' can include an O-Arm® imaging system sold by Medtronic Navigation, Inc. having a place of business in Louisville, CO, USA. The imaging system 138', including the O-Arm® imaging system, or other appropriate imaging systems may be in use during a selected procedure, such as the imaging system described in in U.S. Pat. Nos. 7,188,998; 7,108,421; 7,106,825; 7,001, 045; 6,940,941; 11,344,268; 11,399,784; and U.S. patent application Ser. No. 13/016,718 published on Apr. 26, 2012 as U.S. Pat. App. Pub. No. 2012/0099768, all the above incorporated herein by reference. Further, the imaging system may include various features and elements, such as a slotted filter, such as that disclosed in U.S. Pat. Nos. 10,881, 371 and 11,071,507 to Helm et al., all the above incorporated herein by reference. Other appropriate imaging systems may include C-arm imaging systems including an opposed x-ray source and x-ray detector and related processor modules and/or memory.

As noted above, the suite 130 may include navigation systems, including the various tracking devices 100, 120, 142 that can be tracked with the navigation system including one or more of the tracking systems 104, 108. The tracking information can be used to allow for displaying on the display 62 a pose of an item, e.g., the tool or instrument 34. For example, the graphical representation 34' of the instrument may be displayed alone and/or superimposed on any appropriate image, such as the image of the subject 110. The instrument 34 may be operated, controlled, and/or held by the user 52. The user 52 may be one or more of a surgeon, nurse, welder, etc. Briefly, tracking devices, such as the patient tracking device 100, the imaging device tracking device 142, and the instrument tracking device 120, allow selected portions of the operating theater 130 to be tracked relative to one another with the appropriate tracking system, including the optical localizer 108 and/or the EM localizer 104. It is understood, however, that other tracking modalities may be used such as ultrasound, acoustic, radar, etc. Generally, tracking occurs within a selected reference frame, such as within a patient reference frame.

It will be understood that any of the tracking devices 100, 120, 142 can each be optical, EM tracking devices, or other appropriate tracing device and/or more than one type of tracking device depending upon the tracking localizer used to track the respective tracking devices. It is understood that the tracking devices 100, 120, 14 may all be similar or different and may all be interchangeable but selected or assigned selected purposes during a navigated procedure. It will be further understood that any appropriate tracking system, such as alternative or in addition thereto, tracking system can be used with the navigation system. Alterative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colorado. Exemplary tracking systems are also disclosed in U.S. Pat. No. 7,751,865, issued Jul. 6, 2010; U.S. Pat. No. 5,913,820, issued Jun. 22, 1999; and U.S. Pat. No. 5,592,939, issued Jan. 14, 1997, all incorporated herein by reference.

Further, regarding EM tracking systems it may be necessary to provide shielding or distortion compensation systems to shield or compensate for distortions in the EM field generated by the EM localizer 108. Exemplary shielding systems include those in U.S. Pat. No. 7,797,032, issued Sep. 14, 2010 and U.S. Pat. No. 6,747,539, issued Jun. 8, 2004; distortion compensation systems can include those disclosed in U.S. patent application Ser. No. 10/649,214, filed on Jan. 9, 2004, published as U.S. Pat. App. Pub. No. 2004/0116803, all of which are incorporated herein by reference.

With an EM tracking system, the localizer 108 and the various tracking devices can communicate through an EM controller 105. The EM controller can include various amplifiers, filters, electrical isolation, and other systems. The EM controller 105 can also control the coils of the localizer 104 to either emit or receive an EM field for tracking. A wireless communications channel, however, such as that disclosed in U.S. Pat. No. 6,474,341, issued Nov. 5, 2002, herein incorporated by reference, can be used as opposed to being coupled directly to the EM controller 105.

It will be understood that the tracking system may also be or include any appropriate tracking system, including a STEALTHSTATION® TRIA®, TREON®, and/or S7™ Navigation System having an optical localizer, similar to the optical localizer 108, sold by Medtronic Navigation, Inc. having a place of business in Louisville, Colorado. Further, alternative tracking systems are disclosed in U.S. Pat. No. 5,983,126, issued Nov. 9, 1999, which is hereby incorporated by reference. Other tracking systems include an acoustic, radiation, radar, etc.

Physical space of and/or relative to the subject, such as the patient 20, may be referred to as subject or patient space. Image space defined by an image or coordinate system of an image that is generated or reconstructed with the image data from an imaging system, such as the imaging system 138, 138' may be referred to as image space. The image space can be registered to the patient space by identifying matching points or fiducial points in the patient space and related or identical points in the image space. The imaging device 138, 138' can be used to generate image data at a precise and known position. This can allow image data that is automatically or "inherently registered" to the patient 20 upon acquisition of the image data. Essentially, the position of the patient 20 is known precisely relative to the imaging system 138, 138' due to the accurate positioning of the imaging system 138, 138' in the patient space. This allows points in the image data to be known relative to points of the patient 20 because of the known precise location of the imaging system 138, 138'. It is understood, likewise, that the imaging system may be used to generate image data of the subject 20 at any appropriate time. Further, the imaging system may include one or more of a Magnetic Resonance Imaging (MRI) device, computer tomography (CT) device, etc.

Alternatively, and/or additionally, manual or automatic registration can occur by matching fiducial points in image data with fiducial points on the patient 20. For example, selected patient anatomy (e.g., ear portions, nose tip, brow line, etc.) may be identified in registration of image space to patient space that allows for the generation of a translation map between the patient space and the image space. According to various embodiments, registration can occur by determining points that are substantially identical in the image space and the patient space. The identical points can include anatomical fiducial points or implanted fiducial points. Exemplary tracking and navigation systems and appropriate registration techniques are disclosed in at least one of U.S. Pat. No. 9,737,235 issued Aug. 22, 2017; U.S. Pat. No. 7,751,865 issued Jul. 6, 2010; U.S. Pat. No. 6,474,341 issued Nov. 5, 2002, U.S. Pat. No. 5,913,820 issued Jun. 22, 1999; U.S. Pat. No. 5,592,939 issued Jan. 14, 1997; and/or U.S. Pat. No. 5,983,126 issued Nov. 9, 1999; all of which are incorporated herein by reference.

Once registration has occurred, the navigation system including the tracking systems 104, 108, with and/or including the imaging system 138, 138', can be used during performance of selected procedures. Selected procedures can use the image data generated or acquired with the imaging system 138, 138' and the tracked pose of one or more tracked items can be displayed relative to the image, such as superimposed thereon. The pose that is determined generally includes a selected number of degrees of freedom, such as six degrees of freedom. These may include at least three degrees of location (x, y, and z-axis locations) and orientation (yaw, pitch, and roll). Further, the imaging system 138, 138' can be used to acquire image data at different times relative to a procedure. As discussed herein, image data can be acquired of the patient 20 subsequent to a selected portion of a procedure for various purposes, including confirmation of the portion of the procedure.

An implant may be positioned within the subject 20, including the implant 34. The implant 34 may be positioned within the subject based upon tracking or navigation of the implant 34 relative to the subject 20. Therefore, a tracked position or pose of the implant 34 may be known during the procedure. The tracked location of the implant 34 may be saved to allow a review of the tracked pose of the implant. Therefore, a path and final pose of the implant 34 may be known within the subject 20.

A final pose of the implant 34 may include a final pose of one or more of the electrodes 40, which includes a pose relative to the subject of the electrodes 40. By the known pose of the electrodes 40, a determination or evaluation of a stimulation of the subject 20 relative to the electrodes 40 may be measured. As discussed further herein, the stimulation or neural modulation provided to the subject 20 may be measured or determined. Further an outcome or prognosis of the subject 20 may be determined over time. The determined or tracked outcome of the treatment of the subject 20 may be made and also stored for comparison to the tracked or navigated pose of the implant 34 relative to the subject 20.

As discussed further herein, therefore, the pose of the implant 34 may be related to an outcome for the subject 20. For example, a particular pose, including a location and orientation of one or more of the electrodes 40, may be correlated to an outcome of the subject 20 after treatment and/or during treatment. The correlation may be stored for later analysis and/or planning for a procedure on further subjects, including a current subject. In various embodiments, the pose of the implant 34 may be known for an outcome of the subject, such as a past subject. This may be also determined and stored for a plurality of subjects including related outcomes and poses of the implant 34. After a sufficient or selected number of correlated poses and outcomes have been determined, a planning of a pose of the implant for a subject may include the correlated and stored information to assist in planning a pose of the implant in a later subject that may also be referred to a current subject). This may allow for assistance in planning a pose of the implant and a subject prior to positioning the implant 34 in the subject 20.

Figure 4:
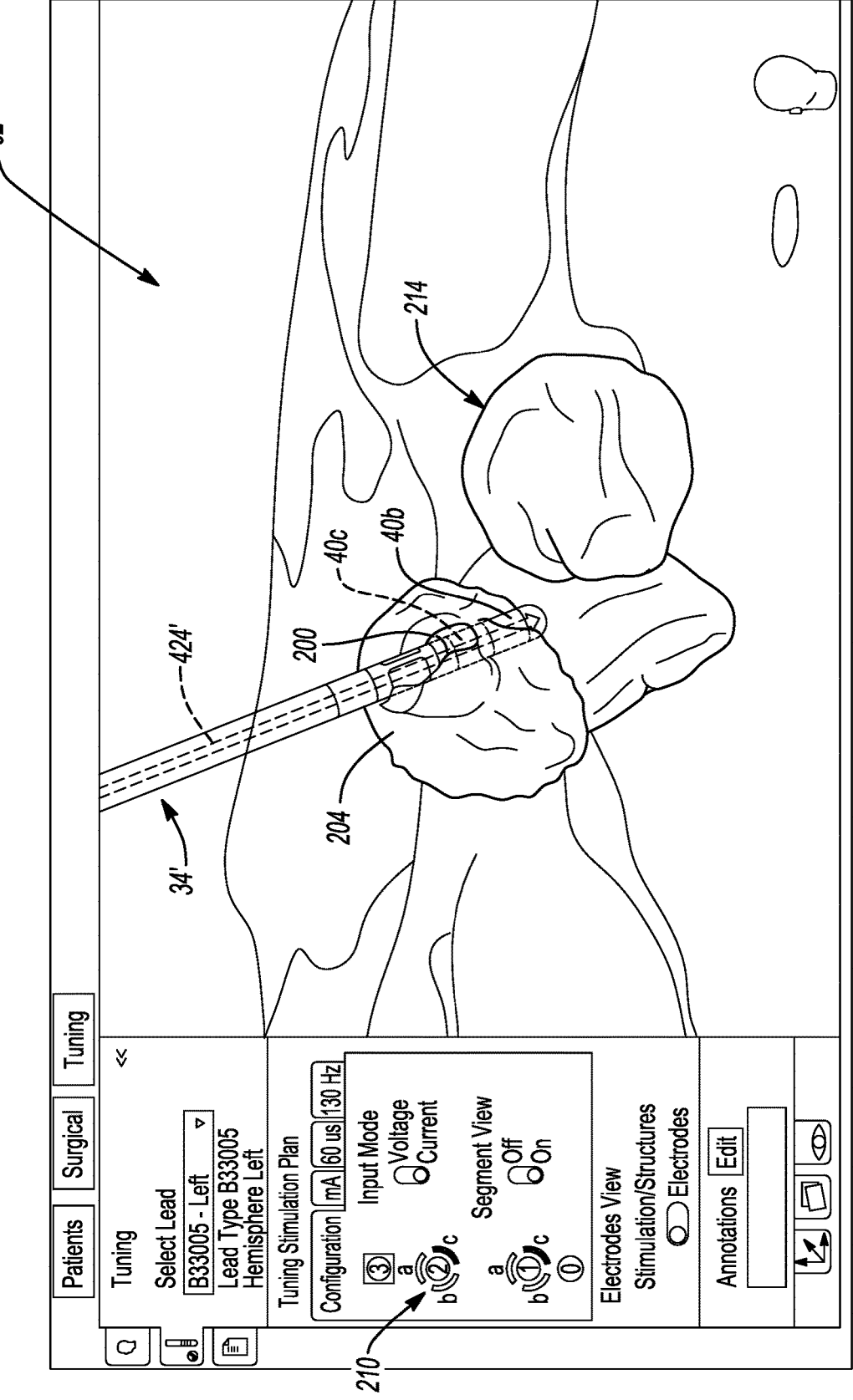
FIG. 4 is a screen shot of a system, according to various embodiments.

Turning reference to FIG. 4, the graphical representation of the implant 34 is displayed on the display device 62 or any appropriate display device. As discussed above, and as generally understood by one skilled in the art, a determination of a possible therapy location within the subject 20 may be made. For example, SureTune® 3 and/or SureTune® 4 software enables the creation of patient-specific anatomy and lead location and orientation based on post procedure data, such as image data sold by Medtronic, Inc. The system may be used to identify an area or volume 200 that is being activated by one or more of the electrodes 40. For example, as illustrated in FIG. 4, one or more of the segments of the segment of electrode 40c may be powered to generate the treatment volume 200, which may also be referred to as the volume of activation and/or VAT. The VAT 200 may be in or near a certain portion of the anatomy of the subject 20 which may also be displayed on the display device 62. Specific anatomy may include a sub-thalamic nucleus (STN) 204. One or more images of the subject may be generated based upon data of the subject for display. Various portions of the image, such as the STN, may also be segmented in the image. Various other portions may also be displayed and/or segmented, such as the red nucleus 214.

While the implant may be positioned relative to any appropriate portion of the subject 20, the STN 204 may be a selected portion. One or more of the electrodes 40 made then be powered to provide the therapy. The therapy may include the VAT. As illustrated in FIG. 4, a graphical user interface (GUI) may include one or more regions to illustrate portions being activated and/or illustrate input provided by the user 52, such as which of the electrodes 40 are operated to generate the VAT 200. The GUI 210 may also illustrate which portions of the electrodes are being activated to form the VAT 200.

The pose of the implant 34 may be determined after implanting in selected subjects, such as a past subject. The past subject may include the current subject 20 in a prior procedure. Similarly, the VAT 200 in the prior subjects may also be determined and displayed, such as with the display 62. Accordingly, after a procedure is performed a pose, including a location and orientation of the electrodes on the implant 34 may be known and may be used to determine the VAT 200. The relationship of the VAT 200 and the location and orientation of electrodes may then be stored for later use, as discussed further herein.

In addition, as noted above, the pose of the implant 34 during implantation may also be determined based upon tracking of a pose of the implant 34. The instrument tracker 120 may be used to track of the pose of the implant 34 with one or more localizers 104, 108. During a procedure, there-fore, the pose of the implant 34 may also be known or determined and illustrated on the display 62. The possible volume of activation 200 may also then be known based upon at the tracked pose of the implant 34 during the implantation. The VAT 200, based upon the pose of the implant 34, may be displayed for use, such as by the user 52. The implant 34 may, therefore, have a real time VAT illustration based upon one or more inputs including which electrode is activated, how it is activated, and the like. It is understood by one skilled in the art and illustrated in FIG. 4, the electrodes may be activated in various manners. For example, one or more of the segments, if available, may be selected for activation or power. The power provided electrodes may then be varied including amperage, a pulse (e.g., length of activation), and a frequency. As noted above variations of the amperage, pulse, and frequency may be used to alter the VAT from one or more of the selected electrodes 40. The VAT may also be varied by varying or changing the electrodes 40 and/or portions thereof that are activated to provide the treatment.

Figure 5:
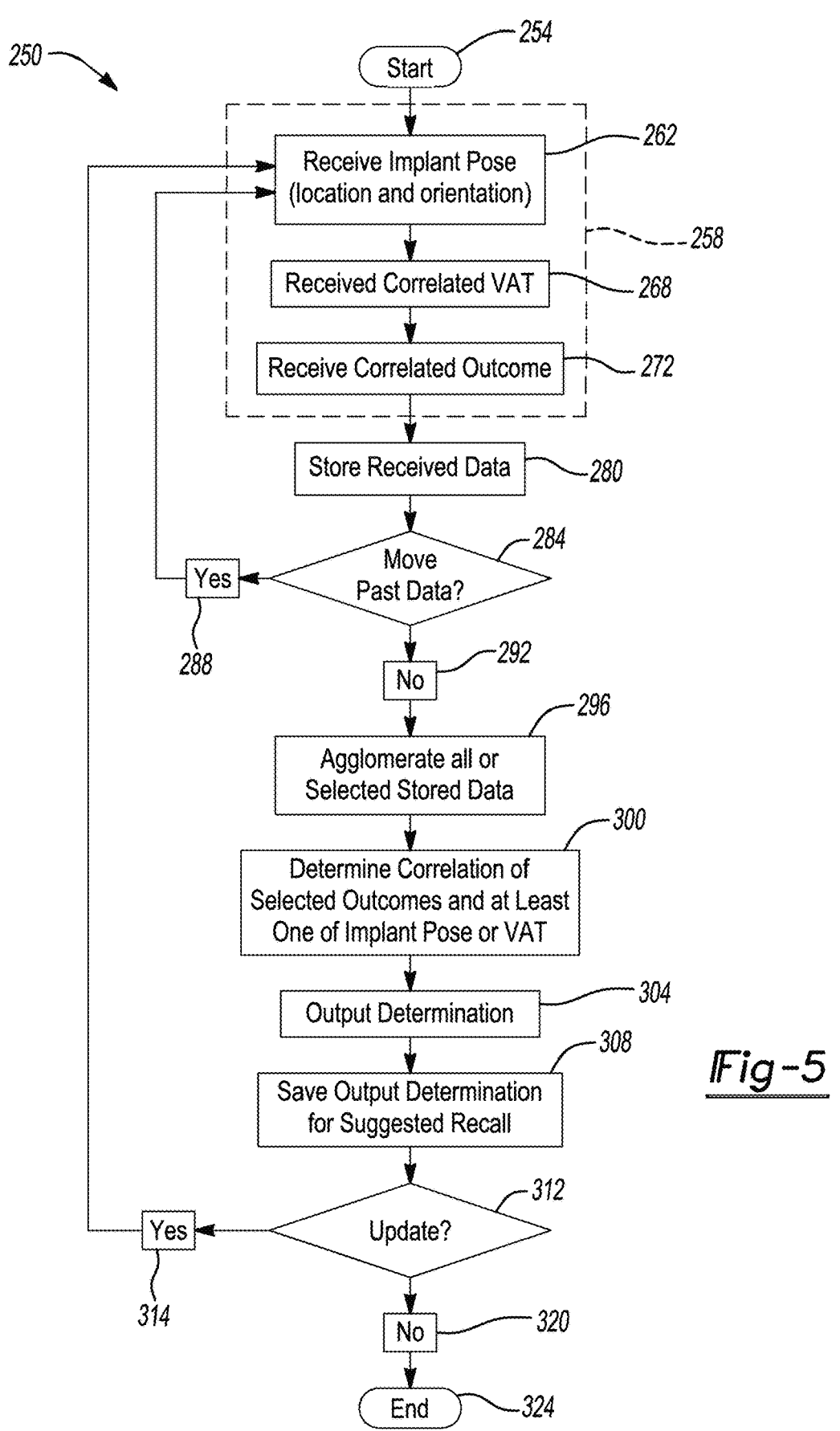
FIG. 5 is a flowchart of a process to determination a correlation of an outcome to inputs related to a procedure, according to various embodiments.

Continuing reference to FIGS. 1 through 4 and with additional reference to FIG. 5, a process 250 to collect and determine correlations of outcomes and determined volume of activations, also referred to as the VAT noted above, is illustrated. The VAT may be determined relative to a selected electrode, as noted above. Further the pose of the electrode may be determined when determining the VAT. This information may be agglomerated and correlated to relate an outcome in the subject 20 to a pose and/or VAT. For example, after positioning and programming of the implant 34, a result of the therapy to the patient 20 may be determined. The result of therapy to the patient 20 may also be referred to as an outcome as applied to the patient. The outcome may be alone and/or in combination with other inputs. Regardless, the outcome of the patient 20 may be determined. The process 250 may be used to determine a correlation between an outcome and one or more of a pose or a VAT that may be output.

Initially, the process 250 may begin in start block 254. After the start block 254, a data collection or receiving process or sub-process 258 may be initiated. The data receiving process includes one or more receipts of data which may be acquired in any appropriate manner and/or order. For example, a user may transmit the data to a selected data collection center. The data may be sent electronically, as a physical data, or the like. Nevertheless, the data may be collected and received for execution of the process 250. In the receiving sub-process 258, the receipt of an implant pose may be made in block 262. The implant pose received in block 262 may include a location and an orientation of the implant 34, one more of the electrodes 40, or any other appropriate portion of the implant 34. The pose of the implant 34 may be useful in recreating or determining the VAT relative to one or more of the activated electrodes during a therapy. Therefore, the pose of the implant received in block 262 may be determined with an appropriate system.

A receiving of a correlated VAT is made in block 268. The correlated or related VAT is related to the implant pose received in block 262. Thus, the VAT may be determined and received in block 268. The VAT may be related to or based upon the pose of the implant received in block 262. Thus, the VAT created in the subject that is received in block 268 and the pose of the implant received in block 262 are known relative to one another.

A received correlated outcome may be received in block 272. The outcome, as noted above, may be based upon various features such as self-determined by the subject 20, determined by clinician, or other appropriate evaluation. The outcome is also related to the VAT received in block 268 and that the implant pose received in block 262. Therefore, a correlation of the relation of the outcome to at least each of the VAT and pose may be received in the process 250.

The received data may be stored in block 280. The data may be stored for any appropriate purpose, such as those discussed further herein. The received data may be stored in any appropriate manner, including those discussed herein but may generally be accessed by a processor module for executing the process 250, as discussed herein. The data may be stored for long-term storage and/or immediate retrieval.

The process 250 may then determine whether more past data is to be collected in the determination block 284. As discussed above, the process 250 may receive data relative to a subject after the implant has been made and an outcome is determined based upon or related to the implant pose and the VAT. Therefore, the process 250 may be understood to be data that is related to a subject prior to a current subject on which a procedure is being performed and/or planned. The past data may be collected or received and used for a current subject, as discussed herein. Further, the past data may be data collected from one or more subjects that are not to be subject 20. For example, data may be collected over a period of time from many subjects that are not to be the current subject. Regardless, more data may be collected by following a YES path 288. Following the YES path 288 flows to receiving of additional data in the receiving sub-process 258.

If no additional data is to be collected, a NO path 292 may be followed. After following the NO path 292, an agglomeration of at least a selected portion of the stored data is made in block 296. The agglomeration of the stored data may be any appropriate agglomeration or correlation process. Appropriate agglomeration processes include building a heat map of outcomes across various locations of the brain. The outcomes may be classified in any appropriate number of classes, such as desirable or undesirable. Other classes may include long-term improvement or short-term improvement. More classes and/or combinations of classes may be made. The outcomes may be collected from a plurality of subjects after an implantation and determined outcome for each subject is made. The location and the outcome may be the stored data. The various locations may be determined relative to one another and/or in an atlas model. The atlas model may then be mapped to a current subject for planning, as discussed herein.

According to various embodiment, an algorithm may agglomerate outcome data to identify a selected target location. The target location may or may not include visualizations for the user to review. The target location may be based on the agglomeration, noted above.

Generally, the agglomeration allows for the data that is stored and selected before the agglomeration or pooling process in block 296. For example, the same or similar poses may be pooled and similar outcomes may be pooled and the related poses and/or VAT as may be related and pooled as well. Regardless, the agglomeration in block 296 allows the data to be further processed as discussed herein.

A determination of a correlation of selected outcomes to at least one of the preceding implant poses or VATs received is made in block 300. The determination of the correlation in block 300 allows for a determination of an outcome that is related to at least one of the received implant poses or the received VAT. The correlation may correlate outcomes that are at a selected threshold, such as those that may be identified as "good" outcomes and/or those that may be identified as "undesirable" outcomes. A threshold difference between the types of outcomes may be made and/or determined based upon the receipt data stored a block 280 for the agglomeration of the data in block 296. The determination allows for a relation of a received pose of the implant from block 262 and/or the received VAT from block 268. The determination of the outcome relates the outcome to at least one of these two which may be used for various processes, such as planning is discussed herein. Therefore, the determination of block 300 allows for a correlation to be determined between the types of outcomes and of the other received data, including the implant pose and at the received VAT.

The correlation, as noted above, may be based on the classified prior outcome for each determined prior location of the implant and/or prior VAT of one or more prior subjects. The one or more prior locations and/or VATs may be co-located relative to one another. For example, their determined location within a selected anatomy (e.g., standard or atlas anatomy). The selected anatomy may be identified in any subject, such as a current subject. The prior outcome may be known and correlated to each prior location and/or VAT within the selected anatomy. The standard anatomy may be correlated to the current subject for planning, as discussed herein.

As disclosed above, the classified outcomes and related locations may be displayed to the clinician with no recommendations made (e.g., a heatmap), allowing the clinician to make a decision based on the consolidated historical data. According to various embodiments, with or without supporting display, a target location for the clinician based on the agglomeration and correlation may be made.

The determination may be output in block 304. The determination output may include a database of selected outcomes. The outcomes may be classified into a plurality of different outcomes, such as different types of outcomes. The classification may include two or more types of outcomes. Outcomes may be determined or classified "good" outcome or a determined or classified "undesirable" outcome in the related received data. For example, a "good" outcome related to a selected one or more received implant poses and the related determination may be output in block 304. Similarly, an outcome may be classified as "undesirable" that is related to another received pose. The output determination may then be stored in block 308 for subsequent recall. The output determination 304 may be stored for recall in block 308 made for various purposes, such as planning a procedure on a subsequent subject, including the current subject. Thus, the determination may be useful for assisting or determining a later pose and VAT.

The process 250 may then determine or may allow for a determination of whether an update is to be made in block 312. Determining to update in block 312 may be a determination as to check whether additional data has been received for determining the correlation in block 300. If the update is determined, a YES path 314 may be followed to receive the additional data in block 258. If no update is to be performed a NO path 320 may be followed to end block 324.

The process 250, therefore, may end in block 324 after outputting and saving for later recall. The process 250 allows for a collection and determination of a correlation based upon the collection of data and classification of outcomes, as noted above. The correlation may be the output and saved for subsequent recall to assist in performing subsequent procedures that are subsequent to the time of the received data. The subsequent procedure may be used or include a planning for a current subject, as discussed further herein.

Figure 6:
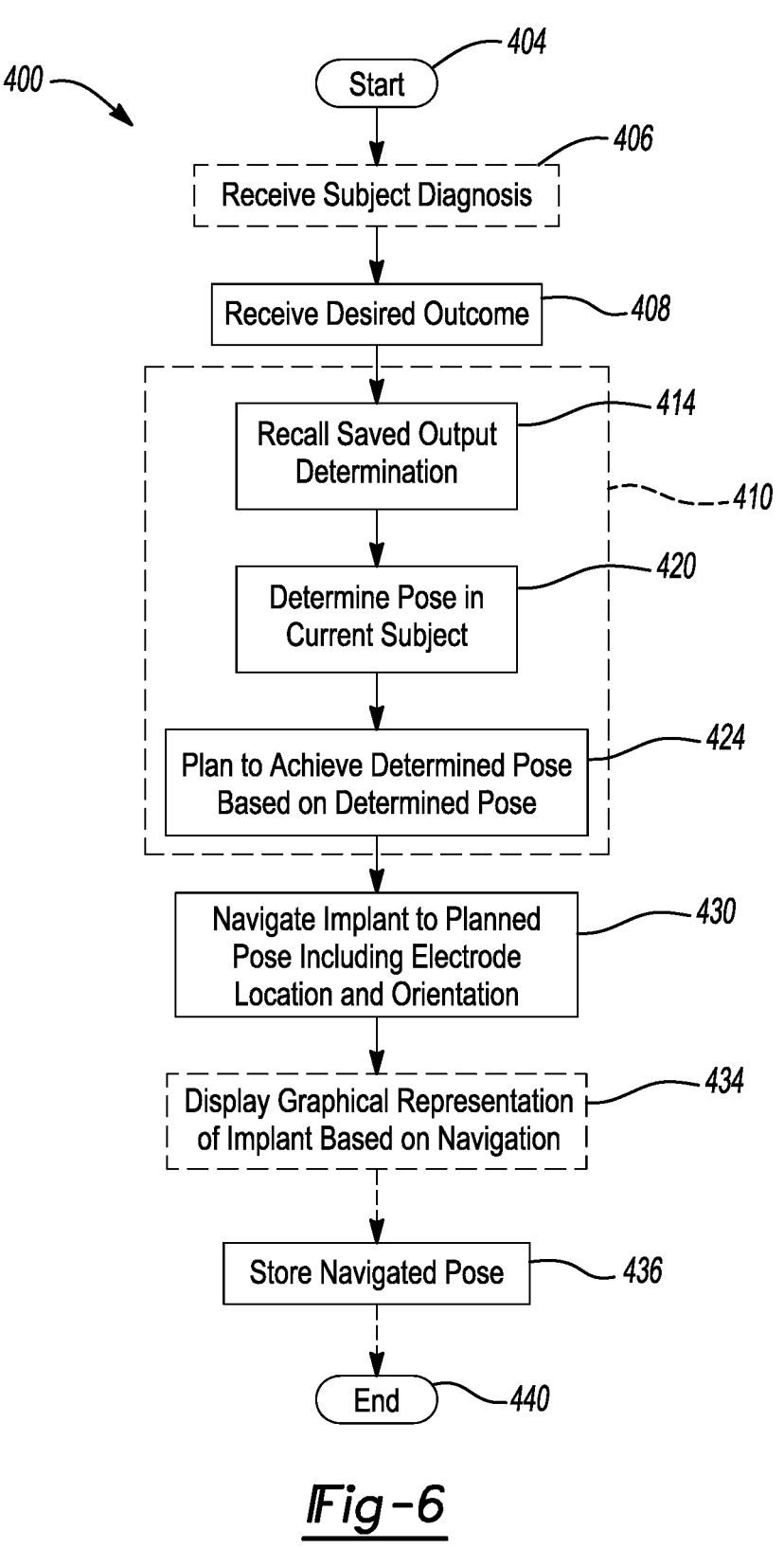
FIG. 6 is a flowchart of a process to plan a procedure based at least in part on a determination of a correlation of an outcome to inputs, according to various embodiments.

Turning reference to FIG. 6, a process 400 is illustrated. The process 400 may use a determination of a correlation of outcome to at least a pose of an implant for procedure. The correlation may be based on at least on the output from the process 250 discussed above including one past patient information and/or agglomerated information. The process 400 may use the prior and/or known information for assisting and/or planning a procedure for a current subject.

Briefly, the process 400 allows for a determined pose related to a selected outcome to be used for planning a procedure and/or performing a procedure on a current subject, such as the subject 20. In using the planning process 400, a user may determine a selected outcome and use the determined pose of the implant related to a prior outcome for planning a procedure. For example, based upon a selected diagnosis of the subject 20 and a selected outcome of the subject 20, the output determination from block 304 of the process 250 may be used to determine a planned pose of the implant 34 in a current subject 20. The planning process 400, therefore, may be used to plan a procedure to position the implant 34 based upon a prior determination, such as a determination from the process 250.

The planning process 400 may begin at start block 404. The process 400 may, optionally, begin with receiving a subject diagnosis in block 406. The subject diagnoses may include or be based on subject data. The diagnosis may include a tumor identification, neurological disorder, or the like. The diagnosis may allow the user 52 to determine and or select an outcome for the subject 20. Further, the diagnosis may include a selected or determined treatment, such as implanting the implant 34 and providing stimulation and/or neuromodulation therewith.

The process 400 may also receive a desired outcome for the subject 20 in block 408. The desired outcome may be any appropriate outcome, such as "good" outcome, as classified above. The desired outcome received in block 408 may be similar and/or identical to outcomes used in the process 250. The received desired outcome in block 408 and the diagnosis in block 406 may be used, as discussed herein, in the process 400 to select and/or plan a pose of an implant in the subject 20.

The planning process may include a planning sub-process 410 that may include various portions or steps, such as those discussed herein, in any appropriate order. For example, the planning process 400 may recall of the output determination in block 414 which may be the output determination from block 304. As noted above, the output determination may be stored for subsequent recall in block 308 and block 414 may include recalling the saved or determined output. The recalled output may be used to determine a pose in a current subject in block 420. The recalled output may be related to at least one of received subject diagnosis in block 406 and/or the received desired outcome in block 408. As noted above, the output includes a correlation of an outcome to at least one of a pose and/or VAT in a prior subject or many prior subjects.

In determining pose of the current subject, the determined correlation of the pose and the desired outcome from block 408 may be used to determine a pose in a current subject 20. For example, as noted above, the implant 34 may be positioned relative to the STN 204. The implant 34, however, includes the plurality of electrodes 40 including possible segmented electrodes 40c. Therefore, an orientation of the electrodes relative to the STN 204 may also be a part of the determined pose for the current subject in block 420. The determined pose may be based upon the determined correlation that is output in block 308 of the process 250 and be used to determine a pose for the current subject in block 420 based upon a selected desired outcome in block 408.

After determining the pose for the current subject in block 420, a plan to achieve the determined pose based on the determine pose may be made in block 424. The plan may include a trajectory of the implant 34 to achieve the pose within the subject 20, a selection of a particular implant, a depth of insertion, and/or other appropriate determinations for the planning. As is understood by one skilled in the art, the implant 34 may include various dimensions, such as a length, diameter, and the like. Various different implants may include different dimensions and may require a different plan. In addition, various instruments may be used to assist in the insertion, such as the Navigus® trajectory guide and/or the overt tach trajectory guide, both sold by Medtronic, Inc. having a place of business in Minnesota. Any appropriate guide, however, may be used to assist in positioning the implant 34 within the subject 20. The plan may include an entry point, an angle for insertion of the implant, positioning of a guide (e.g., Navigus® trajectory guide), etc.

The plan may include selecting an appropriate guide, selecting the appropriate implant, determining the pose within the specific subject 20, or the like. Again, as discussed above and illustrated in FIG. 4, image data of the subject 20 may be displayed on the display device 62. Planning the pose within the current subject 20 may include determining or segmenting the anatomy of the current subject and determining a pose within that specific anatomy. Nevertheless, of the determined correlation of an outcome to a previous pose may assist or be used to determine pose within the current subject.

After planning the pose based upon the determined pose in block 424, the plan may be navigated in block 430. Navigation of the plan in block 430 may include tracking the pose of various portions of the implant 34, such as including a location and/or orientation of the electrode 40. In tracking a location and orientation of the electrode 40, one or more of the electrode contacts may be specifically tracked and/or all may be specifically tracked. As noted above, the electrode 40c may include segments and tracking the pose of the electrode 40c may include tracking the pose of one or more of the segments 40c1, 40c2, and/or 40c3. Thus, the navigation of the implant 34 may be used to assist in ensuring that the implant 34 is implanted within the subject at the planned pose.

The tracking device 120 may be tracked with the appropriate localizer to allow for a determination of the pose of the selected implant including one or more of the electrodes 40. Thus, the user may view the display 62 to view the graphical representation 34' of the implant 34 to determine whether the plan is achieved with of the current tracked pose of the implant 34. The user, therefore, may assist in determining whether the implant 34 should be moved and/or altered to achieve the planned pose.

A graphical representation of the implant may be displayed on the display device 62 in block 434. The display of the graphical representation allows the user 52 to view the current pose that is the tracked pose of the implant 34 in substantially real time. Additionally, one or more planned poses may also be illustrated, such as a planned pose graphical representation 424' (illustrated in FIG. 4). To this end, the user 52 may view the current pose of the implant 34 with a graphical representation 34' relative to the planned trajectory with the graphical representation 424'. This may allow a visual representation and confirmation that the current pose of the implant 34 substantially meets or is within a selected threshold to achieve the planned pose.

The planning process 410, therefore, may be used to plan a procedure based upon the determination that is saved in block 308. The plan may be used to perform a procedure. The procedure may navigate the implant 34 relative to the subject 20. The navigated pose that is planned in block 424 may also be stored in block 436. Storing the navigated pose may further assist in providing data regarding a determined pose after implantation, outcome based upon the navigated pose, or other selected correlations. Therefore, the plan pose and/or the navigated pose may be stored for the correlation in the process 250.

The process 400 may then end in block 440. It is understood that the various processes, including the process 250 and/or the process 400, including the pre-planning process 410 may be incorporated in instructions that are executed by a processor module. The processor module may include a that discussed above and/or any appropriate processor module. The instructions may allow for determining the correlation and/or planning a procedure, as discussed above. While the processing module may generally perform the instructions without additional input, it is understood that the user may provide input, such as selecting a selected or desirable outcome, limitations of implants that are available for planning, and the like. Nevertheless, the processes 250 and 400 may be incorporated into instructions performed by a processing module to assist in providing output for determining a correlation to a selected outcome, planning a procedure, and/or navigating a procedure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a processor and/or a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor, processor module, or module or 'controller' may be replaced with the term 'circuit.' Any of these terms may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of planning a procedure relative to a subject for placing an implant for brain stimulation, the method comprising:

receiving a selected procedure type for the subject;

receiving a selected outcome for the subject;

receiving a determined correlation of the selected outcome to a related pose and volume of activation (VAT) of the implant for brain stimulation based on at least one prior subject;

evaluating received subject data to determine a current subject planned implant pose of the implant for brain stimulation and a planned VAT in the subject that is equivalent to the received determined correlation of the selected outcome to the related pose and VAT of the implant for brain stimulation;

receiving image data of the subject;

receiving real time tracking information of an implant pose associated with an instrument operated by a user relative to the subject during implantation of the implant for brain stimulation; and generating an image, wherein the image comprises a graphical representation of the real time tracking information of the implant pose superimposed on one or more fiducial points associated with the current subject planned implant pose and the image data of the subject.

2. The method of claim 1, wherein generating the image further includes displaying a graphical representation of the current subject planned implant pose relative to a current tracked pose of the implant.

3. The method of claim 1, further comprising: determining a plan including a trajectory of the implant to achieve the current subject planned implant pose.

4. The method of claim 3, further comprising: generating a graphical representation of the determined plan; and outputting the generated graphical representation of the determined plan.

5. The method of claim 1, further comprising: tracking an implant tracking device; and determining a pose of the instrument based on the tracking of the implant tracking device;

wherein receiving tracking information of the implant relative to the subject includes receiving a signal regarding the tracking the implant tracking device.

6. The method of claim 5, wherein tracking the implant tracking device includes providing a localizer configured to at least one of receive a signal from the implant tracking device or transmit a signal to the implant tracking device.

7. The method of claim 6, further comprising:

receiving a tracked pose of a subject tracking device associated with the subject.

8. The method of claim 1, further comprising:

displaying an image of the subject; and superimposing a graphical representation of a current tracked pose of the implant relative to the current subject planned implant pose.

9. The method of claim 1, wherein receiving the selected procedure type includes receiving a diagnosis of the subject.

10. A system for planning a procedure relative to a subject for placing an implant for brain stimulation, the system comprising:

a processor module configured to:

receive a selected procedure type for the subject;

receive a selected outcome for the subject;

receive a determined correlation of the selected outcome to a related pose and volume of activation (VAT) of the implant based on at least one prior subject;

execute instructions to evaluate received subject data to determine a current subject planned implant pose of the implant for brain stimulation and a planned VAT in the subject that is equivalent to the received determined correlation of the selected outcome to the related pose and VAT of the implant for brain stimulation;

receive image data of the subject;

receive real time tracking information of an implant pose associated with an instrument operated by a user relative to the subject during implantation of the implant for brain stimulation; and p2 generate an image, wherein the image comprises a graphical representation of the real time tracking information of the implant pose superimposed on one or more fiducial points associated with the current subject planned implant pose and the image data of the subject; and a display device operable to display the generated image.

11. The system of claim 10, wherein the display device displays the image including a graphical representation of the current subject planned implant pose relative to a current tracked pose of the implant; wherein the processor module is configured to execute instructions to generate the graphical representation.

12. The system of claim 10, wherein the processor module is configured to execute instructions to determine a plan including a trajectory of the implant to achieve the current subject planned implant pose.

13. The system of claim 12, wherein the processor module is configured to execute instructions to: generate a graphical representation of the determined plan; and output the generated graphical representation of the determined plan.

14. The system of claim 10, further comprising: an implant tracking device; and a tracking system to track a pose of the implant tracking device and determine a pose of the instrument based on the tracking of the implant tracking device;

wherein tracking information of the implant relative to the subject includes receiving a signal regarding the tracking the implant tracking device.

15. The system of claim 14, wherein the tracking system includes a localizer configured to at least one of receive a signal from the implant tracking device or transmit a signal to the implant tracking device.

16. The system of claim 15, further comprising: a subject tracking device associated with the subject;

wherein the tracking system is operable to track the subject tracking device.

17. The system of claim 10, further comprising: a display device configured to display an image of the subject;

wherein a graphical representation of a current tracked pose of the implant is superimposed relative to the current subject planned implant pose on the display device.

18. The system of claim 10, wherein the received selected procedure type includes receiving a diagnosis of the subject.

19. A non-transitory computer-readable medium storing a set of instructions, the set of instructions comprising:

one or more instructions that, when executed by one or more processors of a device, cause the device to:

receive a selected procedure type for a subject;

receive a selected outcome for the subject;

receive a determined correlation of the selected outcome to a related pose and volume of activation (VAT) of an implant for brain stimulation based on at least one prior subject;

evaluate received subject data to determine a current subject planned implant pose of the implant for brain stimulation and a planned VAT in the subject that is equivalent to the received determined correlation of the selected outcome to the related pose and VAT of the implant for brain stimulation;

receive image data of the subject;

receive real time tracking information of an implant pose associated with an instrument operated by a user relative to the subject during implantation of the implant for brain stimulation; and generate an image, wherein the image comprises a graphical representation of the real time tracking information of the implant pose superimposed on one or more fiducial points associated with the current subject planned implant pose and the image data of the subject.

20. The non-transitory computer-readable medium of claim 19, wherein the one or more instructions further cause the device to:

determine a plan including a trajectory of the implant to achieve the current subject planned implant pose.

\* \* \* \* \*